United States Patent
Zagorii

(10) Patent No.: US 9,333,207 B2
(45) Date of Patent: May 10, 2016

(54) PHARMACEUTICAL COMPOSITION OF 1-ADAMANTYLETHYLOXY-3-MORPHOLINO-2-PROPANOL OR PHARMACEUTICALLY ACCEPTABLE SALTS THEREOF FOR THE TREATMENT OF CEREBROVASCULAR DISEASE AND NEURODEGENERATIVE DISEASES OF THE CENTRAL NERVOUS SYSTEM

(71) Applicant: Gleb Vladimirovich Zagorii, Kiev (UA)

(72) Inventor: Gleb Vladimirovich Zagorii, Kiev (UA)

( * ) Notice: Subject to any disclaimer, the term of this patent is extended or adjusted under 35 U.S.C. 154(b) by 0 days.

(21) Appl. No.: 14/433,458

(22) PCT Filed: Sep. 17, 2013

(86) PCT No.: PCT/UA2013/000107
§ 371 (c)(1),
(2) Date: Apr. 3, 2015

(87) PCT Pub. No.: WO2014/055055
PCT Pub. Date: Apr. 10, 2014

(65) Prior Publication Data
US 2015/0258098 A1    Sep. 17, 2015

(30) Foreign Application Priority Data

Oct. 5, 2012  (UA) .................. 201211507
Sep. 9, 2013  (UA) .................. 201310843

(51) Int. Cl.
*A61K 31/5375*    (2006.01)

(52) U.S. Cl.
CPC .................. *A61K 31/5375* (2013.01)

(58) Field of Classification Search
None
See application file for complete search history.

(56) References Cited

U.S. PATENT DOCUMENTS

2015/0246051 A1* 9/2015 Zagorii .............. A61K 31/5375
                                                      514/239.2
2015/0265623 A1* 9/2015 Zagorii .............. A61K 31/5375
                                                      514/238.8

FOREIGN PATENT DOCUMENTS

UA          23451 C1    12/1999

OTHER PUBLICATIONS

Ademol-Darnitsa, Normativno-direktivnyc dokumenty MOZ Ukrainy, Nomer registratsionnogo udostovereniia: UA/4845/01/01 on Jul. 26, 2006, retrieved from the Internet <URL: http://mozdocs.kiev.ua/likiview.php?id=5132> on Mar. 16, 2015.
International Searching Authority, International Search Report for International Application No. PCT/UA2013/000107, Dec. 26, 2013, 4 pages, Federal Service for Intellectual Property, Russia.

* cited by examiner

*Primary Examiner* — Michael Barker
(74) *Attorney, Agent, or Firm* — Alston & Bird LLP

(57) ABSTRACT

A pharmaceutical composition for parenteral administration containing the active ingredient 1-adamantylethyloxy-3-morpholino-2-propanol, or pharmaceutically acceptable salts thereof, in a concentration range of from 3 to 100 mg/ml for the treatment of cerebrovascular disease.

2 Claims, No Drawings

PHARMACEUTICAL COMPOSITION OF 1-ADAMANTYLETHYLOXY-3-MORPHOLINO-2-PROPANOL OR PHARMACEUTICALLY ACCEPTABLE SALTS THEREOF FOR THE TREATMENT OF CEREBROVASCULAR DISEASE AND NEURODEGENERATIVE DISEASES OF THE CENTRAL NERVOUS SYSTEM

This application is a national stage application, filed under 35 U.S.C. §371, of International Application No. PCT/UA2013/000107, filed Sep. 17, 2013, which claims priority to Ukrainian Application No. 2012 11507, filed Oct. 5, 2012, and Ukrainian Application No. 2013 10843, filed Sep. 9, 2013, the contents of all of which as are being hereby incorporated by reference in their entirety.

The invention relates to medicine and pharmacy and concerns a pharmaceutical composition for parenteral use comprising 1-adamantylethyloxy-3-morpholino-2-propanol or pharmaceutically acceptable salts thereof as an active within the concentration range of 3-100 mg/ml for treatment of cerebrovascular pathology and neurodegenerative diseases of the central nervous system (CNS).

The pathological states of the brain, such as stroke, chronic cerebrovascular insufficiency, post-hypoxic encephalopathy, and neuroinfections, degenerative brain damages lead to cognitive function impairment (of memory, learning ability, analysis and decision-making), and reducing of human social activity. According to the data of the Ministry of Health of Ukraine within 6 months after acute cerebrovascular accident (ACVA) the hemiparesis is observed in 48% of patients, paralysis in 22%, aphasia in 18%, severe depression in 32%, and 24-53% of patients need complete or partial external assistance.

One of the modern issues of modern medicine klinicheskly in developed countries, including Ukraine, is the problem of cerebrovascular disease (TSVB).

Mortality from TSVB for several decades ranked second overall mortality structure of our population. In Ukraine, as part of cerebrovascular disease ischemic strokes account for 70-85% of cases, bleeding in the brain, 20-25%; subarachnoid hemorrhage 5% of cases.

Current approaches to the treatment of ischemic stroke include recommendations for thrombolysis and early use of anticoagulants (Heparin, Fraxiparine, and Enoxyparin et al.), antiplatelet agents (acetyl acetic acid, clopidogrel, pentoxifylline, etc.). However, their full use during intensive therapy is not always possible due to late diagnosis, falling outside the range of the therapeutic window, occurrence of contraindications and side effects.

Even greater difficulties arise in the case of hemorrhagic stroke (HS) and traumatic brain injury (TBI), especially if it is accompanied by intracranial hemorrhage (including intracerebral). This is preferably associated with the inability of timely neuroimaging for verification of precise diagnosis and selection of further treatment tactics. Similar situation occurs in patients being in coma with severe neurological symptoms. In this situation, without magnetoresonance or computer tomography it is very difficult to clarify the reason of a disturbance of consciousness and neurological deficit—encephalopathy, traumatic brain injury, stroke or another somatic pathology.

The separate nosology group causing ischemic-hypoxic neuronal impairment is neuroinfections, acute and chronic exogenous and endogenous intoxications (infectious-toxic, alcoholic and other types of encephalopathies). It should be noted that such typical pathophysiologic process as hypoxia is an integral part of cerebrovascular disease, and is one of the mechanisms of brain damage leading to irreversible changes in neurons.

Despite the great variety of etiological factors of all the abovementioned states pathobiochemical cascades that occur at that have no significant differences between them allowing to use cerebroprotective drugs in intensive therapy schemes.

To date there is no reference medicinal product (neuroprotective agent) with proven efficacy which can be successfully used as part of undifferentiated therapy, especially in patients with acute cerebral ischemia.

New and promising direction primary cerebroprotection is to develop drugs able to prevent the increasing excitotoxicity by partial blocking NMDA-receptors. The NMDA-receptor antagonists reduce the flow of $Ca^{2+}$ ions into the cell through agonist-dependent calcium channels. It is necessary to consider that complete inactivation of said receptors in vivo leads to extend apoptosis in the CNS enhancing the neurodegenerative processes and blocking the ability of cells to survive under ischemia conditions. The reduced activity of NMDA-receptors prevents necrosis of neuronal cells and excitotoxicity associated with apoptosis. Given that the physiological activity of NMDA-receptors is required for normal functioning of the nervous tissue, the clinical success can only be achieved with NMDA-receptor antagonists that selectively reduce their excessive activation. Among the drugs with the specified mechanism of action, some adamantane derivatives attract attention, including memantine—an agent for treatment of vascular dementia, Alzheimer's disease and multiple sclerosis. This drug is a non-competitive NMDA-receptor antagonist which makes it cerebroprotective, neuroprotective and antiparkinsonian action.

The basis for the development of a pharmaceutical composition for parenteral use comprising the active substance 1-adamantylethyloxy-3-morpholino-2-propanol or pharmaceutically acceptable salts thereof within the concentration range of 3-100 mg/ml is that the drug has the appropriateness of rapid blocking/unblocking NMDA-receptors. The latter may indicate the presence of a protective effect on ischemic brain and makes it promising (as opposed to non-competitive NMDA-receptor blockers) and safer neuroprotective agent.

The object of the claimed invention is making of pharmaceutical composition for parenteral use comprising the active substance 1-adamantylethyloxy-3-morpholino-2-propanol or pharmaceutically acceptable salts thereof within the concentration range of 3-100 mg/ml to increase pharmacotherapy of cerebrovascular pathology and neurodegenerative diseases of various geneses, namely for the treatment of undifferentiated therapy of ischemic and hemorrhagic CVA and after subtype verification in all stroke periods, transient ischemic attacks treatment, open or closed head injury and consequences thereof, encephalopathy of various geneses (alcoholic, infectious-toxic, etc.), hypoxic states of various etiology, post resuscitation disease (state after emergency procedures), treatment and prevention of ischemic brain lesions after thrombolysis, stenting, balloon angioplasty, atheroctomy and removal aneurysms in the internal carotid and vertebral arteries system, diabetic angiopathies and complications thereof.

EXAMPLE 1

Studies in rats have found that using the pharmaceutical composition for parenteral use comprising the active substance 1-adamantylethyloxy-3-morpholino-2-propanol or pharmaceutically acceptable salts thereof in intravenous administration to rats at doses of 3; 30; 50 and 100 mg/kg stimulates the cerebral blood flow in the internal carotid artery system under ACVA model by ischemic and hemorrhagic types.

The ability of the pharmaceutical composition for parenteral use comprising the active substance 1-adamantylethyloxy-3-morpholino-2-propanol or pharmaceutically acceptable salts thereof to improve cerebral blood supply demonstrates the rationale of use thereof both for treatment of undifferentiated ACVA by ischemic and hemorrhagic types and after the subtype verification in all periods of stroke, and for treatment of transient ischemic attacks, open or closed cerebrocranial injury and its consequences.

EXAMPLE 2

Experimental therapy of rats with ischemic ACVA type with the pharmaceutical composition for parenteral use comprising the active substance 1-adamantylethyloxy-3-morpholino-2-propanol or pharmaceutically acceptable salts thereof at a dose of 3 mg/kg once a day for 96 hours of ischemia promoted the normalization of disturbed indices of acid-base balance, oxidative stress and energy metabolism in ischemic brain. The ability of the pharmaceutical composition for parenteral use comprising the active substance 1-adamantylethyloxy-3-morpholino-2-propanol or pharmaceutically acceptable salts thereof to correct changes in metabolic homeostasis of ischemic neurons evidences of appropriateness of its use for treatment of encephalopathy of various geneses (alcoholic, infectious-toxic, etc.), hypoxic states of various etiologies, post resuscitation disease (state after emergency procedures), diabetic angiopathies and complications thereof.

EXAMPLE 3

Experimental treatment of rats with ischemic ACVA with pharmaceutical composition for parenteral use comprising the active substance 1-adamantylethyloxy-3-morpholino-2-propanol or pharmaceutically acceptable salts thereof at a dose of 10 mg/kg once a day for 96 hours of ischemia promoted the reduction of neuronal degradation marker activity (neurospecific enolase) indicating the weakening of destructive changes in ischemic brain with investigated composition, pertaining the structural integrity of neurons and consequent reducing of ischemia focus and penubmra area. This evidences about the appropriateness of the use of the pharmaceutical compositions for parenteral use comprising the active substance 1-adamantylethyloxy-3-morpholino-2-propanol or pharmaceutically acceptable salts thereof for treatment and prevention of ischemic brain lesions after thrombolysis, stenting, balloon angioplasty, atheroctomy and removal of aneurysms in the internal carotid and vertebral arteries system.

EXAMPLE 4

In the study of pharmacological characteristics of aspartate-activated currents and modulation thereof with the pharmaceutical composition for parenteral use comprising the active substance 1-adamantylethyloxy-3-morpholino-2-propanol or pharmaceutically acceptable salts thereof in individual pyramidal hippocampal neurons of 15-day aged white Wistar WAG\GSto rats it was found that studied composition exhibits properties of activator NMDA-receptor-ionofor complex of hippocampal pyramidal neurons with very fast NMDA-receptors blocking/unblocking. This demonstrates the appropriateness of the use of pharmaceutical composition for parenteral use comprising the active substance 1-adamantylethyloxy-3-morpholino-2-propanol or pharmaceutically acceptable salts thereof for the treatment of undifferentiated ACVA of ischemic and hemorrhagic type and after verification subtype in all periods of stroke, transient ischemic attacks treatment, open or closed cerebrovascular injury and consequences thereof, encephalopathy of various geneses (alcoholic, infectious-toxic, etc.), hypoxic states of various etiologies, post resuscitation disease (state after emergency procedures), diabetic angiopathies and complications thereof.

EXAMPLE 5

The experimental treatment of rats with ischemic ACVA pharmaceutical composition for parenteral use comprising the active substance 1-adamantylethyloxy-3-morpholino-2-propanol or pharmaceutically acceptable salts thereof at a dose of 20 mg/kg once a day for 96 hours of ischemia promoted the decrease of endothelial dysfunction and nitrosating stress manifestations. This provides the basis of its use for treatment and prevention of ischemic brain lesions after thrombolysis, stenting, balloon angioplasty, atheroctomy and removal of aneurysms in the internal carotid and vertebral arteries system.

Thus, the results of the studies show that the active substance and pharmaceutical composition for parenteral use comprising the active substance 1-adamantylethyloxy-3-morpholino-2-propanol or pharmaceutically acceptable salts thereof within the concentration range of 3-100 mg/ml have expressed therapeutic properties for different models of cerebrovascular pathology. This gives grounds to use them in clinical practice for treatment as undifferentiated ACVA therapy by ischemic and hemorrhagic type and after subtype verification in all periods of stroke, transient ischemic attacks treatment, open or closed cerebrovascular injury and consequences thereof, encephalopathy of various geneses (alcoholic, infectious toxic, etc.), hypoxic conditions of various etiologies, post resuscitation disease (state after emergency procedures), treatment and prevention of ischemic brain lesions after thrombolysis, stenting, balloon angioplasty, atheroctomy, and removal of aneurysms in the internal carotid and vertebral arteries system, diabetic angiopathies and complications thereof.

The invention claimed is:

1. A method of treating cerebrovascular disease comprising administering a pharmaceutical composition comprising about 3-100 mg/ml of 1-adamantylethyloxy-3-morpholino-2-propanol or pharmaceutically acceptable salts thereof to a patient by parenteral administration, wherein the patient is suffering from one or more of undifferentiated ACVA therapy by ischemic and hemorrhagic type and after subtype verification in all periods of stroke, transient ischemic attacks treatment, open or closed cerebrovascular injury and consequences thereof, encephalopathy of various geneses, hypoxic conditions of various etiologies, post resuscitation disease ischemic brain lesions after thrombolysis, stenting, balloon angioplasty, atheroctomy, and removal of aneurysms in the internal carotid and vertebral arteries system, diabetic angiopathies and complications thereof.

2. The method of treating cerebrovascular disease according to claim 1, wherein the patient is suffering from alcoholic, infectious, or toxic encephalopathy.

* * * * *